(12) United States Patent
Choi et al.

(10) Patent No.: US 11,715,581 B2
(45) Date of Patent: Aug. 1, 2023

(54) ELECTRIC FIELD SHAPING APPARATUS AND TARGET PROCESSING DEVICE USING ELECTRIC FIELD

(71) Applicant: UIF (University industry Foundation), Yonsei University, Seoul (KR)

(72) Inventors: Heon Jin Choi, Seoul (KR); Jae Suk Sung, Gyeonggi-do (KR)

(73) Assignee: UIF (UNIVERSITY INDUSTRY FOUNDATION), YONSEI UNIVERSITY, Seoul (KR)

( * ) Notice: Subject to any disclaimer, the term of this patent is extended or adjusted under 35 U.S.C. 154(b) by 0 days.

(21) Appl. No.: 17/183,929

(22) Filed: Feb. 24, 2021

(65) Prior Publication Data
US 2022/0270781 A1 Aug. 25, 2022

(30) Foreign Application Priority Data
Feb. 25, 2020 (KR) .......................... 10-2020-0022825

(51) Int. Cl.
*H01B 7/02* (2006.01)
*A61N 1/04* (2006.01)

(52) U.S. Cl.
CPC .............. *H01B 7/02* (2013.01); *A61N 1/0456* (2013.01); *A61N 1/0472* (2013.01)

(58) Field of Classification Search
CPC ....... H01B 7/02; A61N 1/0456; A61N 1/0472
USPC ....................................................... 361/230
See application file for complete search history.

(56) References Cited

U.S. PATENT DOCUMENTS

| | | | | |
|---|---|---|---|---|
| 5,448,133 A | * | 9/1995 | Ise | H01J 31/127 313/308 |
| 6,153,969 A | * | 11/2000 | Levine | H01J 3/022 313/309 |
| 8,744,316 B2 | * | 6/2014 | Morino | G03G 15/025 250/326 |
| 2002/0030438 A1 | * | 3/2002 | Ito | H01J 3/022 445/24 |
| 2003/0137236 A1 | * | 7/2003 | Tuck | H01J 1/304 313/495 |

(Continued)

FOREIGN PATENT DOCUMENTS

KR 1020010106479 A 11/2001
KR 1020170106363 A 9/2017

OTHER PUBLICATIONS

Yokoyama, et al. "The mechanism of the stabilisation of glow plasma at atmospheric pressure", Journal of Physics D: Applied Physics, 1990.

(Continued)

*Primary Examiner* — Timothy J Thompson
*Assistant Examiner* — Michael F McAllister
(74) *Attorney, Agent, or Firm* — Tarolli, Sundheim, Covell & Tummino L.L.P

(57) ABSTRACT

An electric field shaping apparatus according to a present embodiment includes a substrate, a first electrode positioned on the substrate, a second electrode spaced apart from the first electrode, a power source configured to provide a voltage between the first electrode and the second electrode, and an insulating material with which the first electrode is coated, wherein one or more holes configured to shape an electric field generated between the first electrode and the second electrode are formed in the insulating material.

11 Claims, 5 Drawing Sheets

(56) References Cited

U.S. PATENT DOCUMENTS

| | | | | |
|---|---|---|---|---|
| 2003/0193297 | A1* | 10/2003 | Russ | H01J 3/021 |
| | | | | 315/169.3 |
| 2008/0194169 | A1* | 8/2008 | Sterling | H01L 21/68785 |
| | | | | 445/73 |
| 2013/0035731 | A1* | 2/2013 | Hackler | A61N 1/0456 |
| | | | | 607/2 |
| 2014/0083856 | A1* | 3/2014 | Sideris | G01N 27/44713 |
| | | | | 204/600 |
| 2016/0011526 | A1* | 1/2016 | Xie | G03F 7/70325 |
| | | | | 355/53 |
| 2016/0067706 | A1* | 3/2016 | Molho | B01L 3/502792 |
| | | | | 204/601 |
| 2016/0357107 | A1* | 12/2016 | Buchberger, Jr. | G03F 7/70866 |
| 2017/0309770 | A1* | 10/2017 | Colli | H01L 31/035218 |
| 2017/0326558 | A1* | 11/2017 | Mahshid | B03C 5/005 |

OTHER PUBLICATIONS

Korean Office Action for Application No. 10-2020-0022825 dated Apr. 19, 2021.

* cited by examiner

ELECTRIC FIELD SHAPING APPARATUS AND TARGET PROCESSING DEVICE USING ELECTRIC FIELD

This application claims priority to and the benefit of Korean Patent Application No. 10-2020-0022825, filed on Feb. 25, 2020, the disclosure of which is incorporated herein by reference in its entirety.

BACKGROUND

1. Field of the Invention

The present invention relates to an electric field shaping apparatus and a target processing device using an electric field.

2. Discussion of Related Art

Many studies are being conducted to obtain new characteristics of a target and a region adjacent to the target by forming an electric field in a small area, stimulating the target using energy of the electric field, and changing properties thereof. These studies are being conducted not only on inorganic materials but also on organic materials and biomaterials such as cells.

In addition, studies are also being actively conducted on the field of treating nerve-related problems by emitting energy to nerve tissue of the human body to stimulate the nerve tissue and reduce pain.

SUMMARY OF THE INVENTION

In a method of providing energy to a target using an electric field, a voltage is applied between two electrodes to generate an electric field, and the electric field is provided to a target disposed between the electrodes. The energy of the electric field changes properties of the target or stimulates the target.

However, since a magnitude of the electric field is proportional to a magnitude of the voltage applied to the electrode, a high voltage should be applied to the electrode to obtain a high electric field. Accordingly, high power is necessary to obtain high energy. In addition, it is difficult to emit energy to only a specific region because an electric field has a property of spreading in a wide area.

The present invention is directed to providing an apparatus capable of shaping an electric field and concentrating energy of the electric field to a target region to obtain high energy.

According to an aspect of the present invention, there is provided an electric field shaping apparatus including a substrate, a first electrode positioned on the substrate, a second electrode spaced apart from the first electrode, a power source configured to provide a voltage between the first electrode and the second electrode, and an insulating material with which the first electrode is coated, wherein one or more holes configured to shape an electric field generated between the first electrode and the second electrode are formed in the insulating material.

The one or more holes may expose a surface of the first electrode.

The one or more holes may be formed to have different depths.

The insulating material may be divided into a plurality of regions, and one or more of depths, cross-sectional areas, shapes, and the number of the holes formed in one region may be different from one or more of depths, cross-sectional areas, shapes, and the number of the holes formed in another region.

One or more of the first electrode and the second electrode may be formed of any one among gold, copper, silver, platinum, and nickel.

The insulating material may be any one material among polyimide (PI), polycarbonate (PC), polyethylene terephthalate (PET), silicone, Teflon, alumina, and glass.

According to another aspect of the present invention, there is provided an electric field shaping apparatus including a substrate, a first electrode positioned on the substrate, a second electrode spaced apart from the first electrode, a power source configured to provide a voltage between the first electrode and the second electrode, an insulating material with which the first electrode is coated and in which one or more holes are formed, and a holder which is positioned between the first electrode and the second electrode and on which a target to be processed by an electric field generated between the first electrode and the second electrode is positioned.

The one or more holes may expose a surface of the first electrode.

The one or more holes may be formed to have different depths.

The insulating material may be divided into a plurality of regions, and one or more of depths, cross-sectional areas, shapes, and the number of the holes formed in one region may be different from one or more of depths, cross-sectional areas, shapes, and the number of the holes formed in another region.

One or more of the first electrode and the second electrode may be formed of any one among gold, copper, silver, platinum, and nickel.

The insulating material may be any one material among polyimide (PI), polycarbonate (PC), polyethylene terephthalate (PET), silicone, Teflon, alumina, and glass.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
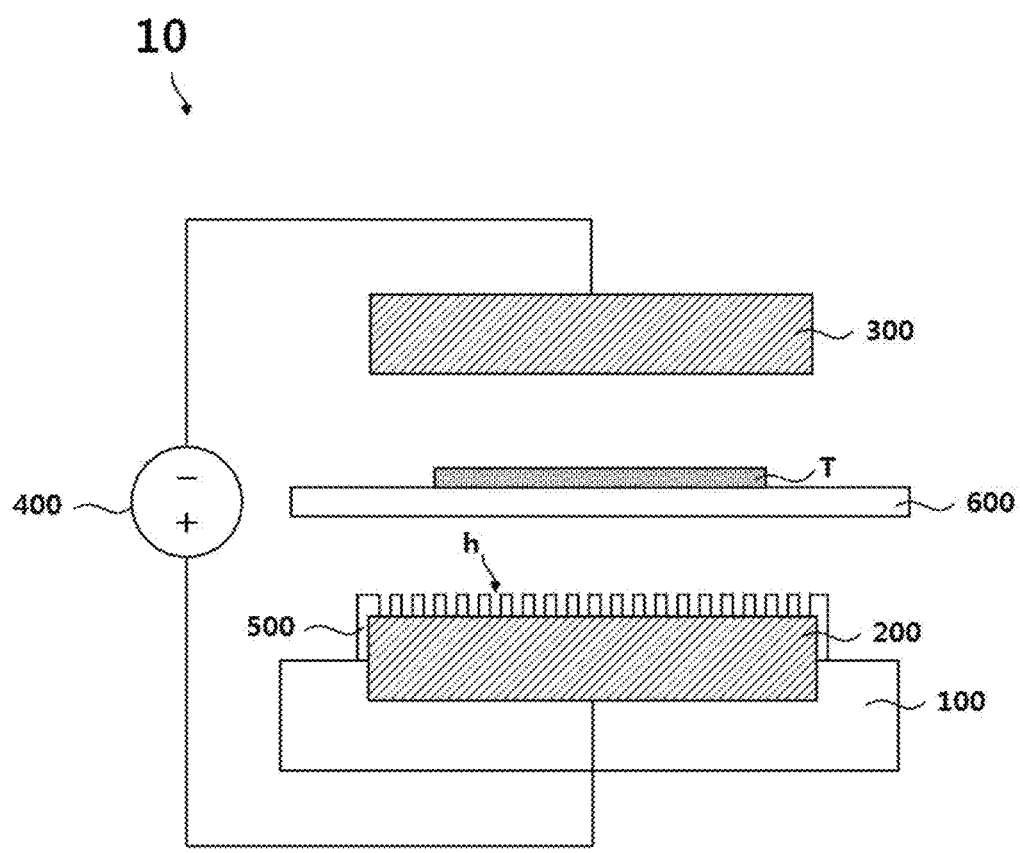
FIG. 1 is a schematic cross-sectional view illustrating an electric field shaping apparatus according to an embodiment of the present invention.

Hereinafter, an electric field shaping apparatus and a target processing device using the same according to embodiments of the present invention will be described with reference to the accompanying drawings. FIG. 1 is a schematic cross-sectional view illustrating an electric field shaping apparatus 10 according to an embodiment of the present invention. Referring to FIG. 1, the electric field shaping apparatus 10 according to the present embodiment includes a substrate 100, a first electrode 200 positioned on the substrate 100, a second electrode 300 spaced apart from the first electrode 200, a power source 400 configured to provide a voltage between the first electrode 200 and the second electrode 300, and an insulating material 500 for coating the first electrode 200, and one or more holes h for shaping an electric field formed between the first electrode 200 and the second electrode 300 are formed in the insulating material 500.

As an example, the electric field shaping apparatus 10 according to the present embodiment may further include a holder 600 which is positioned between the first electrode 200 and the second electrode 300 and on which a target T to be processed by an electric field generated between the first electrode 200 and the second electrode 300 is positioned.

The electric field shaping apparatus 10 may function as a process apparatus which processes the target T held by the holder 600 using a shaped electric field.

The first electrode 200 may be positioned on the substrate 100. As an example, the substrate 100 may be formed of an insulating material and may be an insulating synthetic resin substrate including glass, polycarbonate (PC), flame retardant (FR)-4, polyimide (PI), or polyethylene terephthalate (PET), a Teflon substrate, an alumina substrate, or a silicon substrate.

The first electrode 200 and the second electrode 300 are disposed to be spaced apart from each other and connected to the power source 400 configured to provide a voltage. Each of the first electrode 200 and the second electrode 300 may be formed of a conductive metal such as gold, copper, silver, platinum, or nickel. The first electrode 200 and the second electrode 300 may be connected to the power source 400 to receive the voltage and may generate an electric field using the provided voltage.

In the example illustrated in FIG. 1, the power source 400 is illustrated as a direct current (DC) power source 400, and an electric field formed in this case is formed in a direction from the first electrode 200 toward the second electrode 300. In an example which is not illustrated in the drawings, the power source 400 may be an alternating current (AC) power source, and a direction of an electric field generated by the first electrode 200 and the second electrode 300 may be alternately changed according to a pole of a voltage provided by the alternating current power source.

The first electrode 200 is coated with the insulating material 500. As an example, the insulating material 500 may be a material such as PI, PC, PET, silicone, Teflon, alumina, or glass. The holes h may be formed in the insulating material 500 through a photolithography method, a laser perforation method, a silk screen printing method, an inkjet printing method, or the like.

Figure 2A:
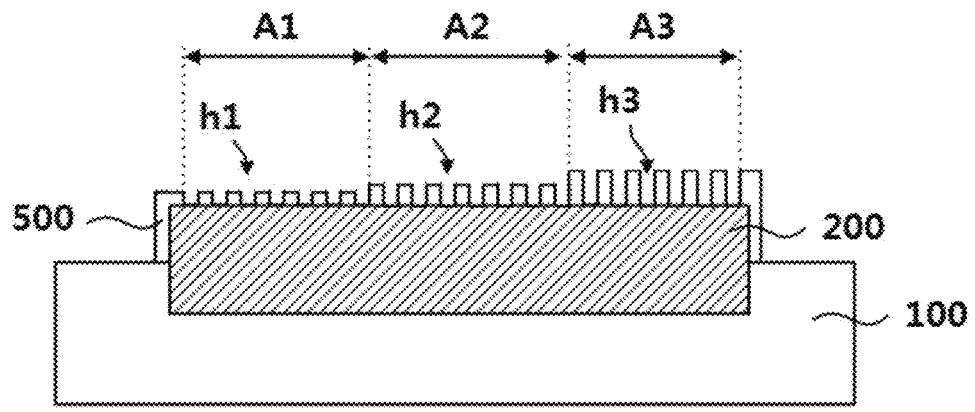
FIG. 2A is a cross sectional view for describing an example of holes (h) formed in an insulating material (500) for coating a first electrode (200)
Figure 2B:
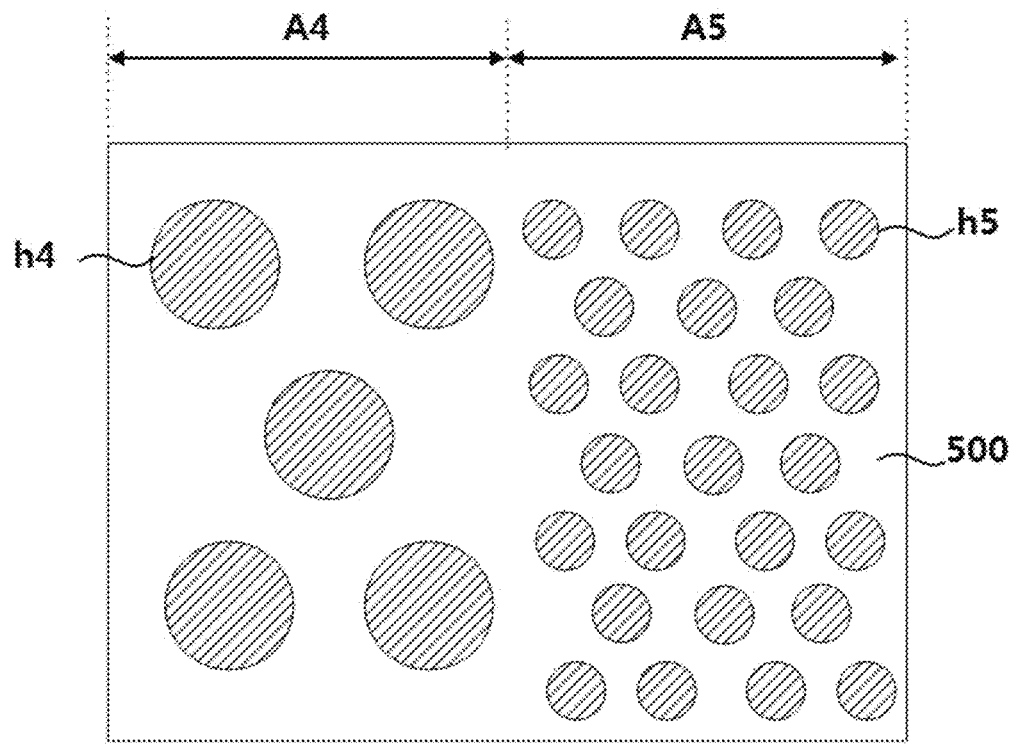
FIG. 2B is a plane view for describing an example of holes (h) formed in an insulating material (500) for coating a first electrode (200)

FIGS. 2A-B is a set of views for describing examples of the holes h formed in the insulating material 500 for coating the first electrode 200. Referring to FIG. 2A, the insulating material 500 for coating the first electrode 200 may be divided into a plurality of regions A1, A2, and A3. Holes h1, h2, and h3 which are different from each other may be formed in the regions. The holes h1, h2, and h3 formed in the plurality of regions A1, A2, and A3 expose a surface of the first electrode 200, and heights of the holes h1, h2, and h3 may be different.

As an example, the holes h1 of which depths are relatively small may be formed in a first region A1, and the holes h2 of which depths are relatively larger than the depths of the holes h1 formed in the first region A1 may be formed in a second region A2. In addition, the hole h3 having the largest depth may be formed in a third region A3.

As the depths of the holes become larger, a magnitude of an electric field may be increased. That is, a magnitude of an electric field generated in the first region A1 in which the hole h1 has the smallest depth may be greater than a magnitude of an electric field generated in the second region A2 in which the hole h2 has the depth larger than the depth of the hole h1 formed in the first region A1. In addition, the magnitude of the electric field generated in the second region A2 may be greater than a magnitude of an electric field generated in the third region A3 in which the hole h3 having the largest depth is formed.

FIG. 2B is a plan view illustrating an upper surface of a portion of the insulating material 500 for coating the first electrode 200 when viewed from above. Referring to FIG. 2B, the surface of the insulating material 500 may be divided into a plurality of regions A4 and A5. Holes h4 having large cross-sectional areas may be formed in the region A4, and the relatively large number of holes h5 having cross-sectional areas relatively smaller than cross-sectional areas of the holes h4 of the region A4 may be formed in the region A5 when compared to the region A4.

In an example which is not illustrated in the drawings, a plurality of holes may be formed in the insulating material 500, and cross-sectional areas and/or shapes thereof may be different from each other.

Referring to FIG. 1 again, in the embodiment illustrated in FIG. 1, the holder 600 on which the target T is positioned may be formed between the first electrode 200 and the second electrode 300. The holder 600 capable of holding the target T may be formed between the first electrode 200 and the second electrode 300. The holder 600 may be formed of a material, such as glass, PC, FR4, PI, PET, Teflon, or alumina, which does not block or absorb an electric field.

The target T is a target object to which an electric field is provided and which is processed by the provided electric field and may be formed of an inorganic or organic material. In addition, the target T may be formed of a biomaterial such as cells, neurons, spheroids, or organoids stimulated by an electric field.

Figure 3A:
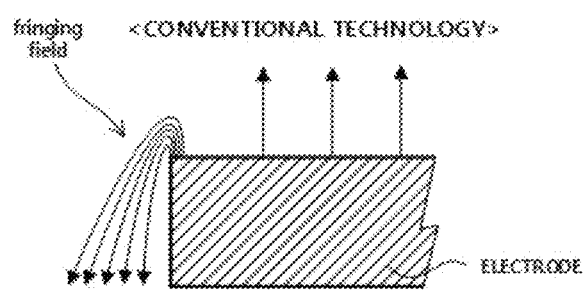
FIG. 3A is a schematic view illustrating an electric field formed in an electrode structure according to a conventional technology.
Figure 3B:
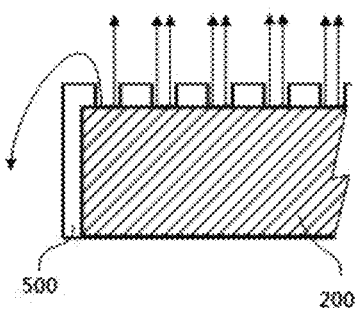
FIG. 3B is a schematic view illustrating an electric field formed according to the embodiment of the present invention.

Hereinafter, an operation of the electric field shaping apparatus 10 having the above-described structure will be described. FIG. 3A is a schematic view illustrating an electric field formed in an electrode structure according to a conventional technology, and FIG. 3B is a schematic view illustrating an electric field formed according to the embodiment of the present invention. Referring to FIG. 3A, when a voltage is applied to an electrode according to the conventional technology, an electric field is formed. Since the electric field having a higher density is generated as a region has a small curvature radius, a fringing field is formed at a corner of the electrode structure formed as illustrated in FIG. 3A to have a density which is higher than a density of a fringing field formed on a surface of a flat electrode. Accordingly, a high voltage should be applied to a flat surface portion using the power source in order to increase a density of an electric field generated at the flat surface portion occupying a majority of an area of an electrode, a very high electric field is locally generated at an edge portion in which a curvature radius is small, and thus there is a problem in that a distribution of the electric field is not uniform.

However, referring to FIG. 3B in which the electric field generated by the electrode structure according to the present embodiment is schematically illustrated, since an edge portion of the first electrode 200 is coated with the insulating material 500, generation of a fringing field at the edge portion in which a curvature radius is small may be reduced, and an electric field may be induced through the holes h formed in the insulating material 500. Accordingly, an advantage is provided in which the electric field may be shaped to have a target shape between the first electrode 200 and the second electrode 300 by adjusting the depths and the number of the holes h.

In addition, there are advantages in that the electric field with a higher efficiency may be provided to the target T positioned on the holder 600, and a distribution of the electric field may be uniformly shaped even when a low voltage is provided unlike the conventional technology.

Simulation Result

Figure 4A:
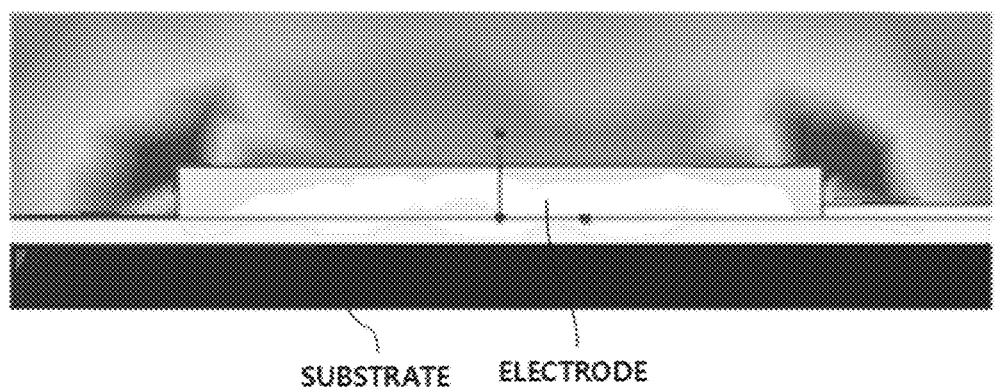
FIG. 4A is a view illustrating a magnitude of the electric field generated in the electrode structure according to the conventional technology.
Figure 4B:
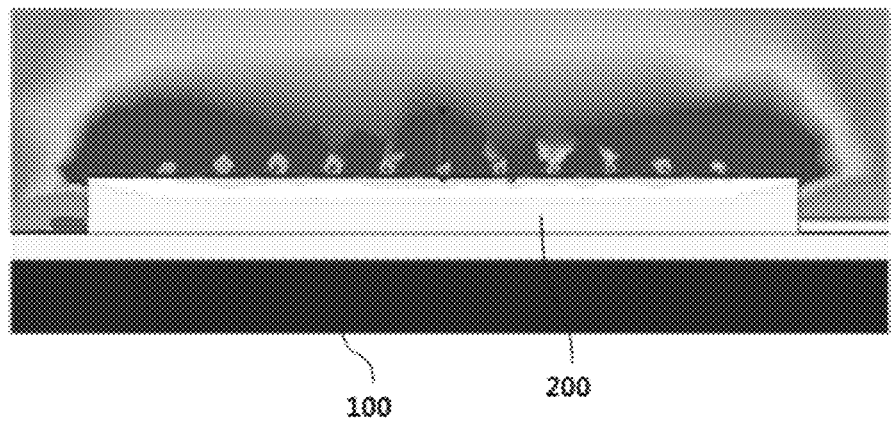
FIG. 4B is a view illustrating a magnitude of the electric field generated by an electrode structure according to the embodiment of the present invention for comparison.

Hereinafter, a simulation example in which the electric field shaping apparatus is implemented will be described with reference to FIGS. 4 and 5. FIG. 4A is a view illustrating a magnitude of an electric field generated in the electrode structure according to the conventional technology. FIG. 4B is a view illustrating a magnitude of an electric field generated by the electrode structure according to the embodiment of the present invention for comparison. Referring to FIG. 4A, it may be seen that an electric field having a magnitude of 300 V/m is formed at a flat portion of an electrode and an electric field having a magnitude of 800 V/m is formed at an edge of the electrode according to the conventional technology. This is because a fringing field is generated at an edge portion in which a curvature radius is small as described above.

However, according to the present embodiment illustrated in FIG. 4B, it may be seen that an electric field having a magnitude of 800 V/m is generated at each of a flat portion and an edge portion of the electrode. This is based on a fact that generation of a fringing field is suppressed by the holes formed in the insulating material 500 for coating the first electrode 200. In addition, it may be seen that the electric field may be shaped upward from the electrode by the holes formed in the insulating material 500.

Figure 5A:
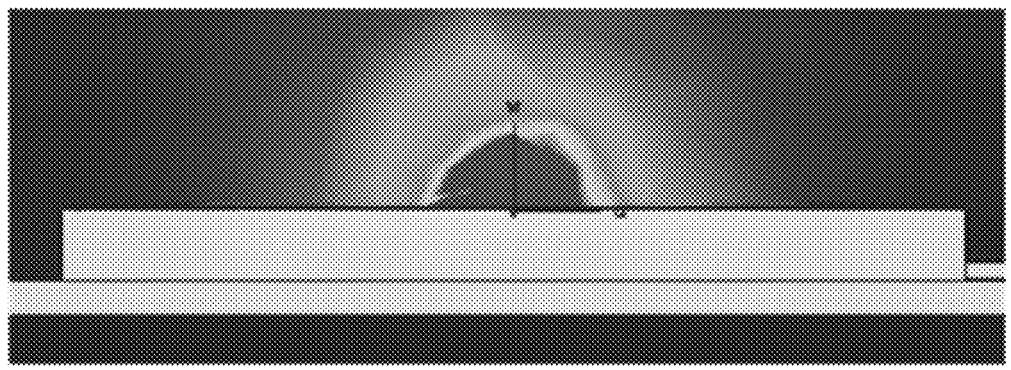
FIG. 5A is a view illustrating a magnitude of an electric field in a case in which the first electrode (200) is coated with the insulating material (500) and a single hole is formed in the insulating material (500)
Figure 5B:
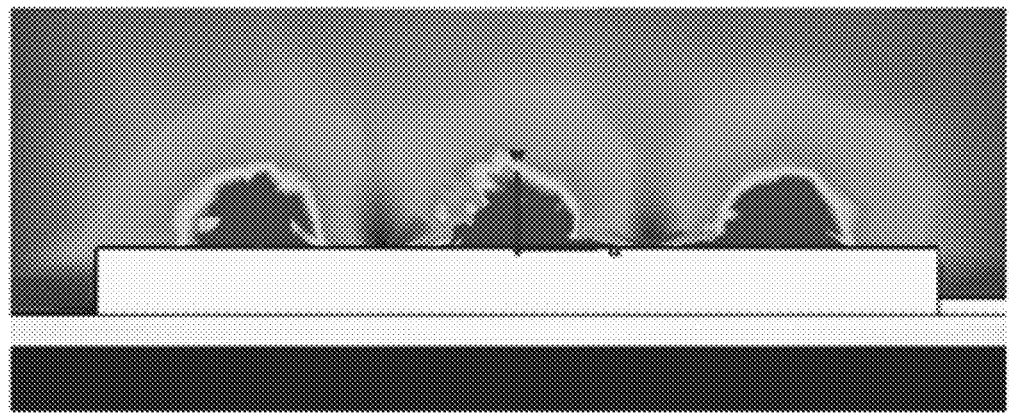
FIG. 5B is a view illustrating a magnitude of an electric field in a case in which the first electrode (200) is coated with the insulating material (500) and three holes are formed in the insulating material (500).

FIG. 5A is a view illustrating a magnitude of an electric field in a case in which the first electrode 200 is coated with the insulating material 500 and a single hole is formed in the insulating material 500, and FIG. 5B is a view illustrating a magnitude of an electric field in a case in which the first electrode 200 is coated with the insulating material 500 and three holes are formed in the insulating material 500. Referring to FIGS. 5A and 5B, a fact that generation of a fringing field is commonly suppressed at the edge of the electrode may be seen, and a magnitude of an electric field is increased in a direction toward a center of the hole.

In addition, in an example illustrated in FIG. 5A, in a case in which a single hole is formed, it may be seen that the magnitude of the electric field is 15,000 V/m, which is about 20 times the magnitude of the electric field of an example illustrated in FIG. 4B so that energy of the electric field is concentrated. This is an effect in that only one hole is formed to minimize an area of the exposed electrode so as to concentrate limited energy.

In an example illustrated in FIG. 5B, the magnitude of the electric field is shown in the case in which three holes are formed. It may be seen that energy of the electric field is distributed to a plurality of regions in which the holes are formed, and a value of the energy of the electric field is 10,000 V/m which is greater than a value of the energy in the case of FIG. 4B in which the plurality of holes are formed and smaller than a value of energy in the case of FIG. 5A. Accordingly, a distribution and a magnitude of energy may be adjusted by adjusting the number of holes.

That is, it may be seen that the magnitude and the shape of the electric field may be adjusted by coating the electrode with the insulating material and forming the holes in the insulating material, and the electric field of which the magnitude and the shape are adjusted may be provide to the target so that an electric field processing may be performed on the target.

According to the present embodiment, there are advantages in that an electric field can be shaped to provide energy of the electric field to a target region and a target can be processed using the electric field.

The present invention has been described with reference to the embodiment illustrated in the accompanying drawings to aid in understanding of the present invention, but these are only examples for implementing the present invention. It will be understood by those skilled in the art that various modifications and equivalent other example embodiments may be made. Therefore, the scope of the present invention is defined by the appended claims.

What is claimed is:

1. An electric field shaping apparatus comprising:
   a substrate;
   a first electrode positioned on the substrate;
   a second electrode spaced apart from the first electrode;
   a power source configured to provide a voltage between the first electrode and the second electrode; and
   an insulating material with which the first electrode is coated,
   wherein one or more holes configured to shape an electric field generated between the first electrode and the second electrode are formed in the insulating material,
   wherein the insulating material is divided into a plurality of regions; and
   wherein one or more of depths, cross-sectional areas, shapes, and the number of the holes formed in one region are different from one or more of depths, cross-sectional areas, shapes, and the number of the holes formed in another region.

2. The electric field shaping apparatus of claim 1, wherein the one or more holes expose a surface of the first electrode.

3. The electric field shaping apparatus of claim 1, wherein one or more of the first electrode and the second electrode are formed of any one among gold, copper, silver, platinum, and nickel.

4. The electric field shaping apparatus of claim 1, wherein the insulating material includes any one material among polyimide (PI), polycarbonate (PC), polyethylene terephthalate (PET), silicone, Teflon, alumina, and glass.

5. An electric field shaping apparatus comprising:
   a substrate;
   a first electrode positioned on the substrate;

a second electrode spaced apart from the first electrode;

a power source configured to provide a voltage between the first electrode and the second electrode;

an insulating material with which the first electrode is coated and in which one or more holes are formed; and a holder which is positioned between the first electrode and the second electrode and on which a target to be processed by an electric field generated between the first electrode and the second electrode is positioned.

6. The electric field shaping apparatus of claim 5, wherein the one or more holes expose a surface of the first electrode.

7. The electric field shaping apparatus of claim 5, wherein the one or more holes are formed to have different depths.

8. The electric field shaping apparatus of claim 5, wherein the one or more holes are formed to have different cross-sectional areas or shapes.

9. The electric field shaping apparatus of claim 5, wherein:

the insulating material is divided into a plurality of regions; and one or more of depths, cross-sectional areas, shapes, and the number of the holes formed in one region are different from one or more of depths, cross-sectional areas, shapes, and the number of the holes formed in another region.

10. The electric field shaping apparatus of claim 5, wherein one or more of the first electrode and the second electrode are formed of any one among gold, copper, silver, platinum, and nickel.

11. The electric field shaping apparatus of claim 5, wherein the insulating material includes any one material among polyimide (PI), polycarbonate (PC), polyethylene terephthalate (PET), silicone, Teflon, alumina, and glass.

* * * * *